United States Patent
Kang

(10) Patent No.: US 8,157,733 B2
(45) Date of Patent: Apr. 17, 2012

(54) BLOOD PRESSURE MEASUREMENT APPARATUS

(75) Inventor: Hee-Jung Kang, Ansan-si (KR)

(73) Assignee: Daeyo Medi Co., Ltd., Ansan-si, Gyeonggi-do (KR)

( * ) Notice: Subject to any disclaimer, the term of this patent is extended or adjusted under 35 U.S.C. 154(b) by 599 days.

(21) Appl. No.: 12/377,344

(22) PCT Filed: Aug. 23, 2007

(86) PCT No.: PCT/KR2007/004051
§ 371 (c)(1),
(2), (4) Date: Feb. 12, 2009

(87) PCT Pub. No.: WO2008/023950
PCT Pub. Date: Feb. 28, 2008

(65) Prior Publication Data
US 2010/0069764 A1    Mar. 18, 2010

(30) Foreign Application Priority Data

Aug. 25, 2006 (KR) .................. 10-2006-0081186
Aug. 23, 2007 (KR) .................. 10-2007-0085050

(51) Int. Cl.
A61B 5/02 (2006.01)

(52) U.S. Cl. ..................... 600/301; 128/900

(58) Field of Classification Search .............. None
See application file for complete search history.

(56) References Cited

U.S. PATENT DOCUMENTS

| 5,255,686 A | 10/1993 | Takeda |
| 6,432,060 B1 | 8/2002 | Amano |
| 6,932,772 B2 | 8/2005 | Kan |
| 7,048,691 B2 * | 5/2006 | Miele et al. .......... 600/504 |

* cited by examiner

Primary Examiner — Shafiqul Haq
(74) Attorney, Agent, or Firm — Sherr & Vaughn, PLLC

(57) ABSTRACT

The present invention relates to a blood pressure measurement apparatus comprising: an input unit where at least one value selected from the maximum applied pressure, which is the applied pressure at which the maximum pulse pressure is attained during the pulse pressure measurement at the measurement part, the maximum pulse pressure, which is the pulse pressure at the maximum applied pressure, the depth of blood vessel at the measurement part measured by a pressure sensor, the elasticity of skin tissue at the measurement part and the elasticity of blood vessel at the measurement part is inputted; and a mean arterial pressure calculation unit where the mean arterial pressure is calculated from the input values of the maximum applied pressure, the depth of blood vessel and the elasticity of skin tissue. The present invention offers more effective and reliable blood pressure measurement apparatus.

11 Claims, 5 Drawing Sheets

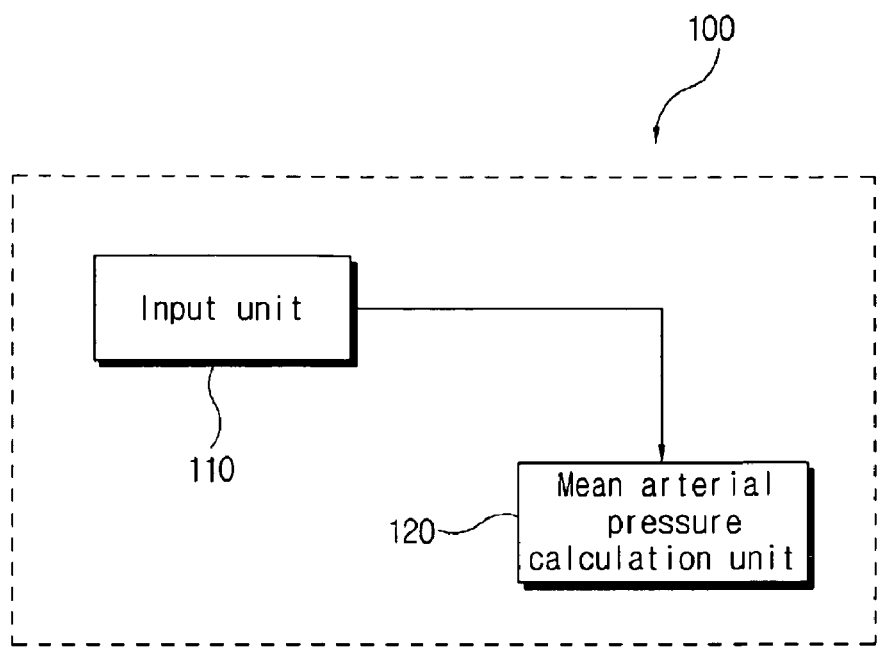
[Fig. 1]
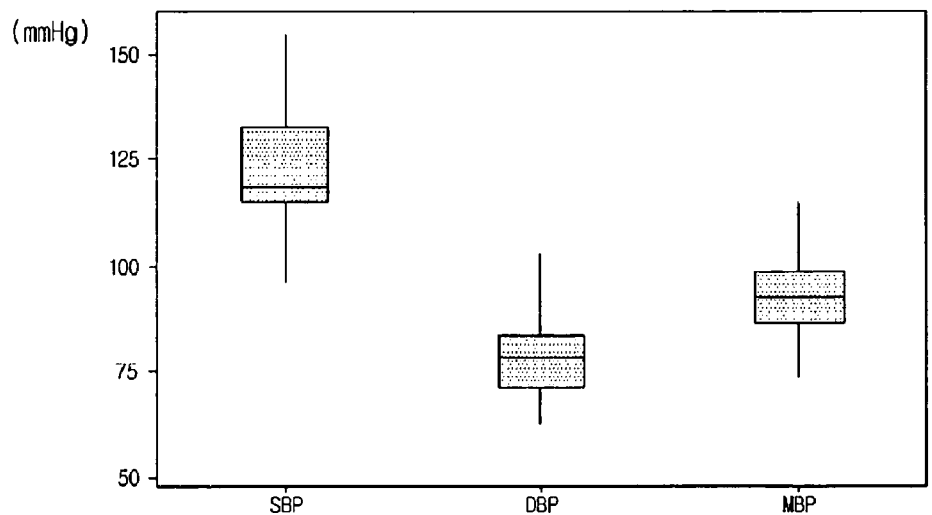
[Fig. 2]
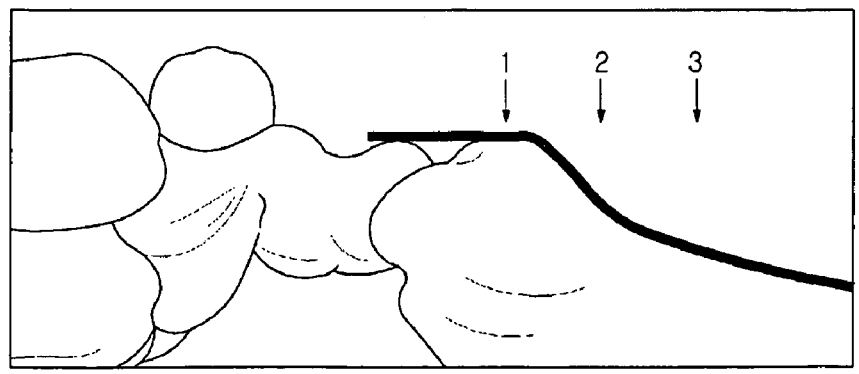
[Fig. 3]

[Fig. 4]
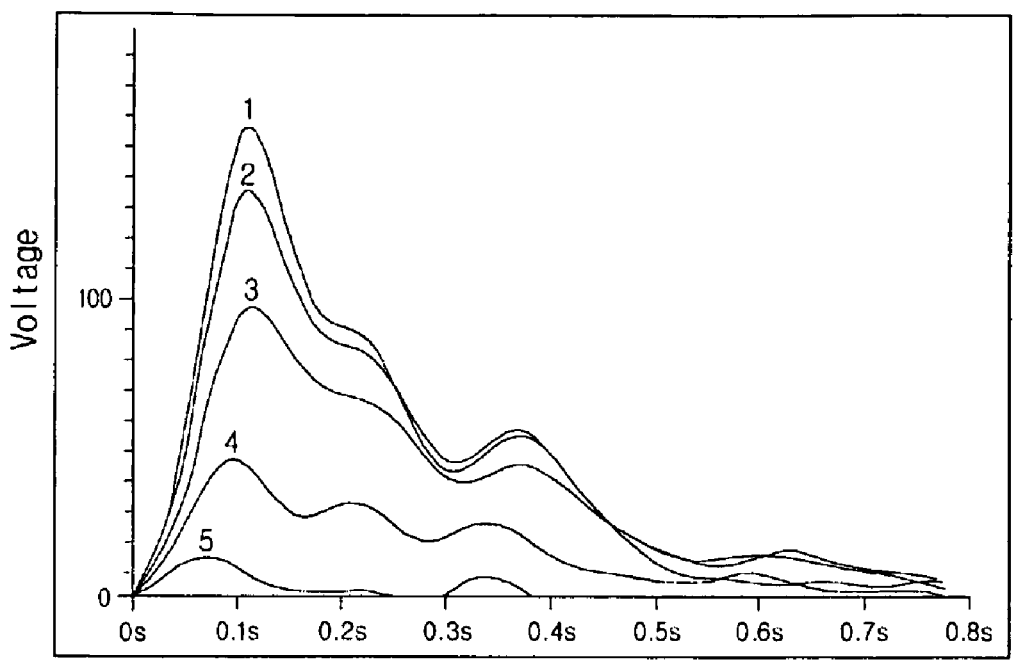
[Fig. 5]
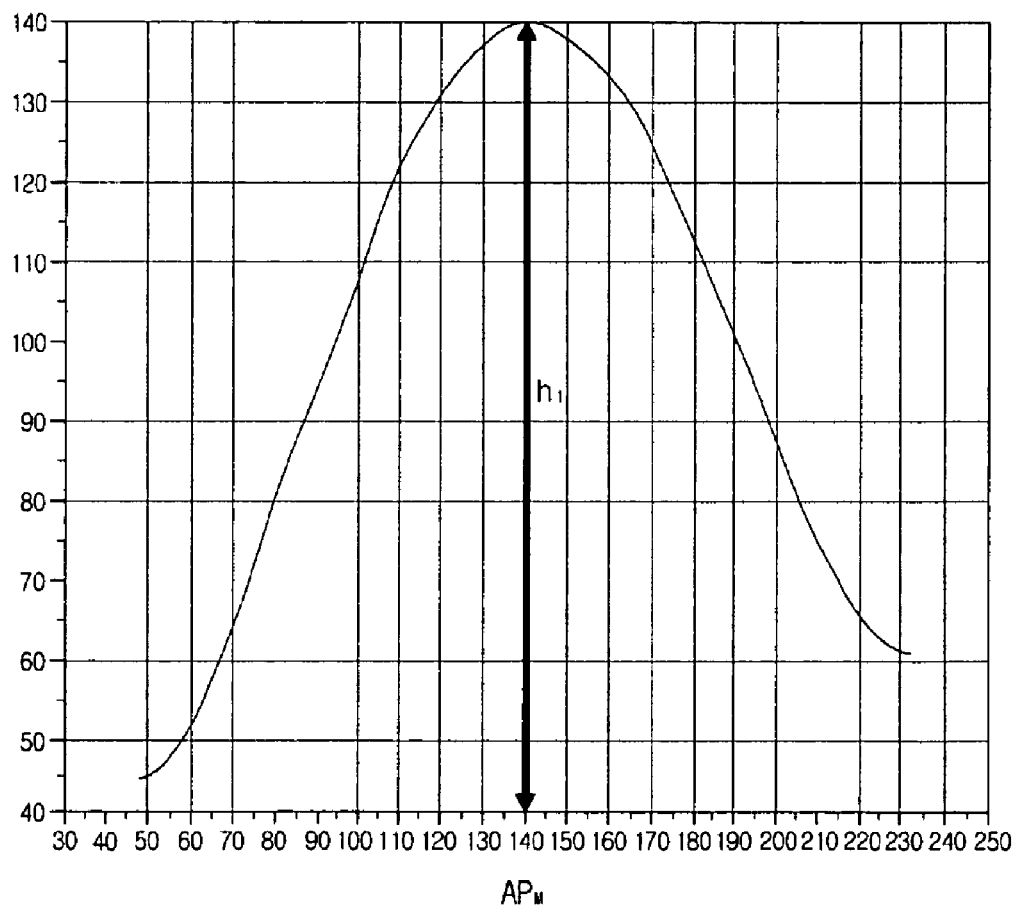

[Fig. 6]
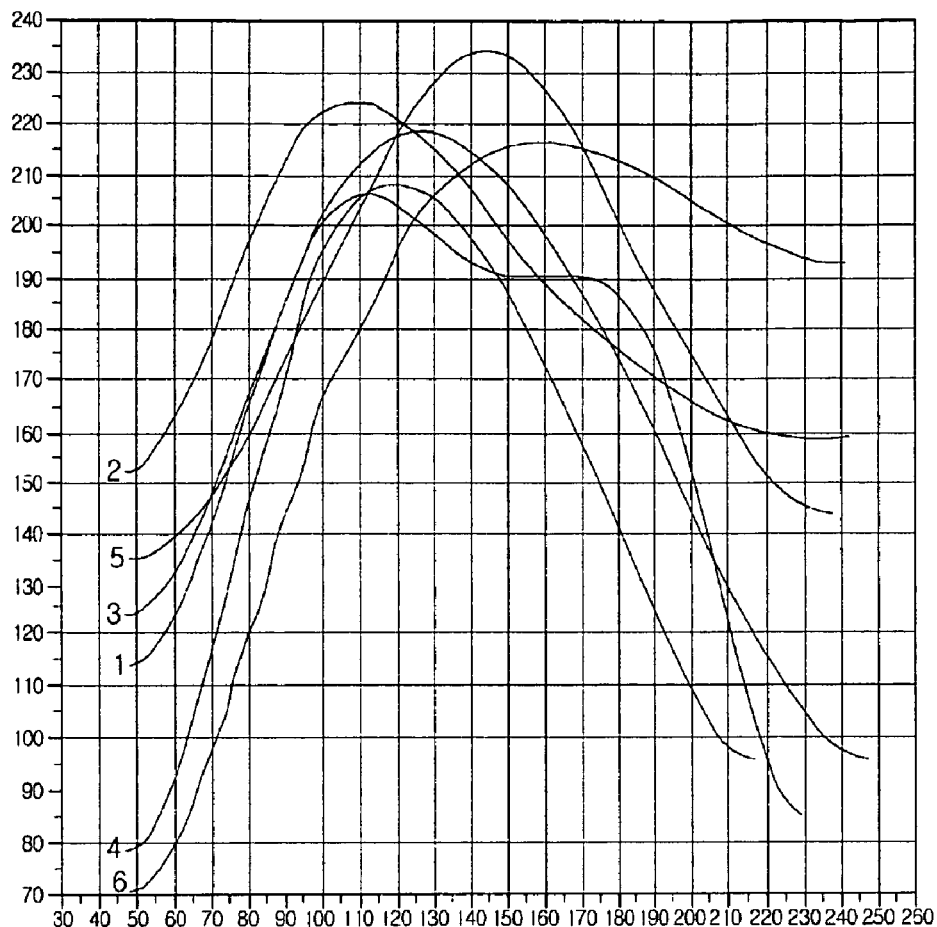
[Fig. 7]
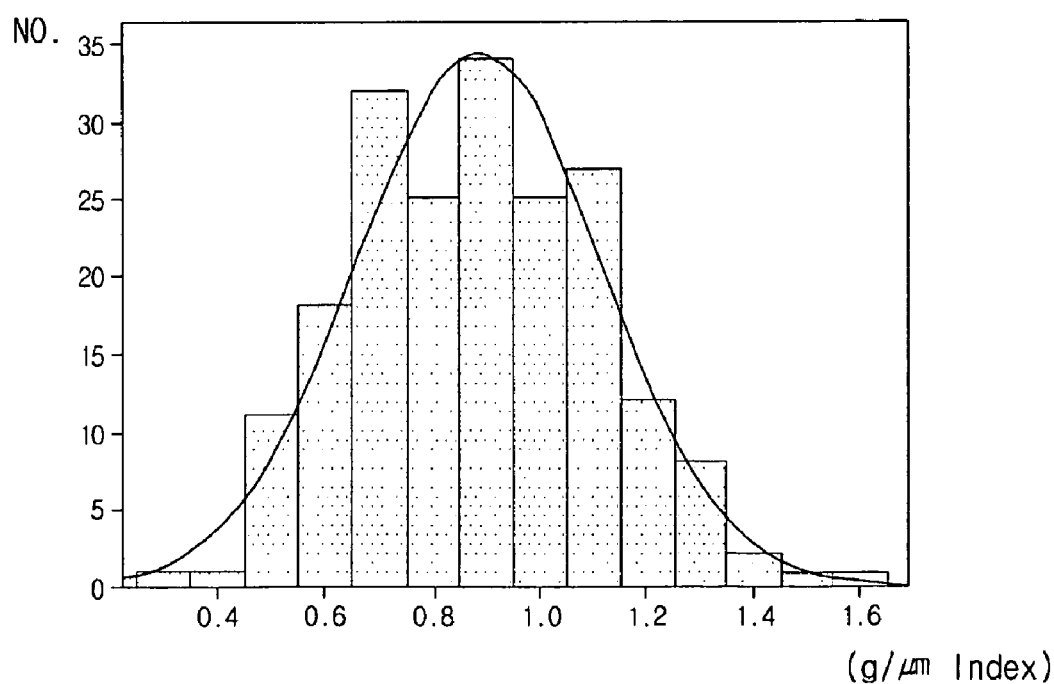

[Fig. 8]
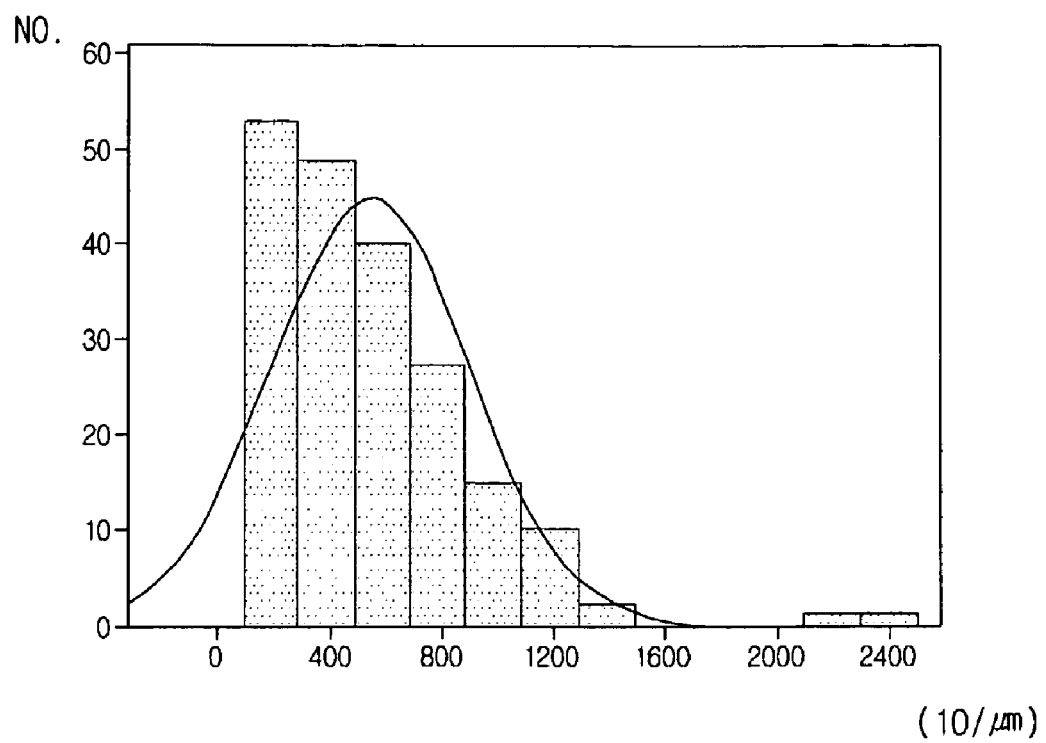
(10/μm)
[Fig. 9]
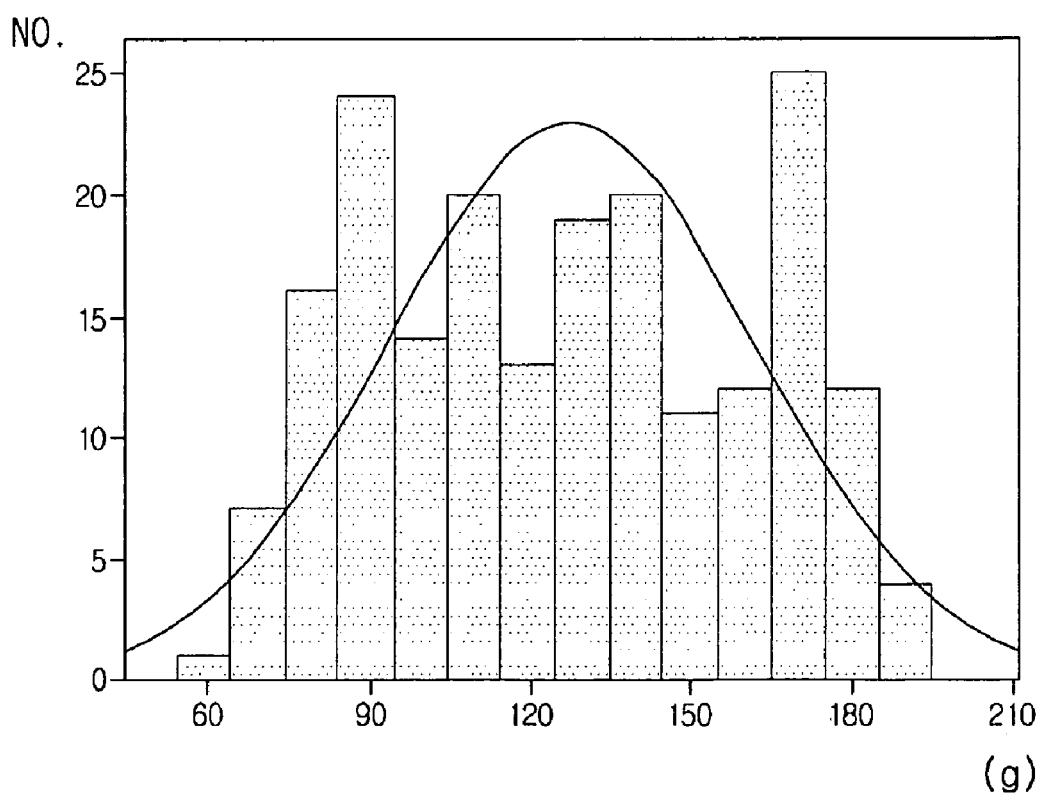
(g)

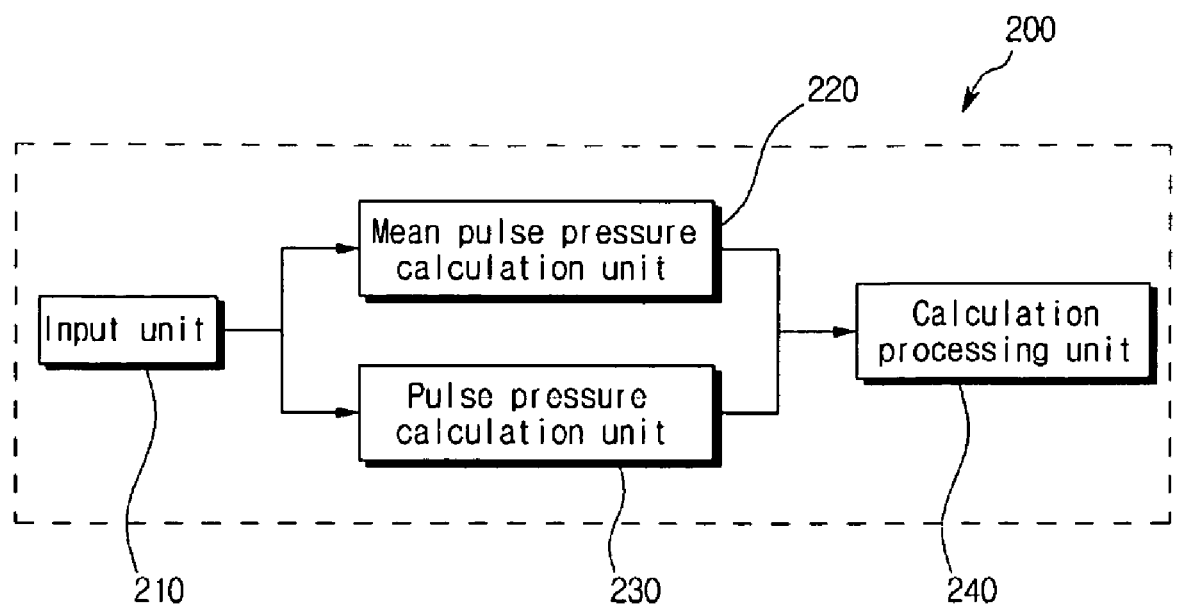
[Fig. 10]

BLOOD PRESSURE MEASUREMENT APPARATUS

The present application claims priority to Korean Patent Application No. 10-2006-0081186 (filed on Aug. 25, 2006), Korean Patent Application No. 10-2007-0085050 (filed on Aug. 23, 2007) and PCT International Patent Application No. PCT/KR2007/004051 (filed on Aug. 23, 2007) which are hereby incorporated by reference in their entirety.

TECHNICAL FIELD

The present invention relates to a blood pressure measurement apparatus, more particularly to a blood pressure measurement apparatus enabling more convenient and exact measurement of blood pressure.

BACKGROUND ART

In general, blood pressure can be measured invasively or non-invasively.

A typical example of the invasive method is directly measuring the pressure of the peripheral artery by inserting a catheter. However, this method involves the risk of arterial bleeding and is improper for the frequent measurement for physical checkup.

A typical example of the non-invasive method is one using a mercury manometer. Such a blood pressure measurement using a mercury manometer is performed as follows. The measurement part is pressed and the pulse is sensed with a stethoscope or fingers, while slowly releasing the pressure. And then the blood pressure can be measured from the height of the column of mercury corresponding to the pulse starting point and pulse end point.

Another non-invasive method is the oscillometric method. In the oscillometric method, a cuff is placed around the upper arm or wrist and inflated until the artery is completely occluded. And then slowly releasing the pressure in the cuff, the values of the pressure oscillation in the cuff is sensed by the pressure sensor and recorded to measure the blood pressure.

In the blood pressure measurement by the non-invasive method, the mean arterial pressure can be calculated by the following Math FIG. 3:

$$MAP=DBP+(SBP-DBP)/3 \quad \text{[Math Figure 3]}$$

where, MAP is mean arterial pressure, DBP is diastolic blood pressure, SBP is systolic blood pressure, and (SBP−DBP) is pulse pressure (PP).

However, the blood pressure measurement using the non-invasive method is restricted in that a continuous measurement is impossible since the cuff needs to be inflated and deflated.

Recently, a blood pressure measurement apparatus which enables a continuous non-invasive blood pressure measurement was developed.

However, the apparatus is complicated because it measures a blood pressure using an electrocardiogram (ECG) and a photoplethysmograph (PPG). Further, because the blood pressure has to be measured at various parts of the body, the patients may feel unpleasant. In addition, the accuracy of the blood pressure measurement tends to be dependent upon the precision of the two devices.

DISCLOSURE OF INVENTION

Technical Problem

The present invention has been made to solve the aforesaid problems and an object of the invention is to provide a blood pressure measurement apparatus providing comfort for patients, requiring no cuff and offering effective and reliable measurement of the systolic blood pressure and the diastolic blood pressure, as well as the mean arterial pressure.

Technical Solution

The blood pressure measurement apparatus according to the present invention provides comfort for patients, requires no cuff and offers complete, effective and reliable measurement of the blood pressure including the systolic blood pressure and the diastolic blood pressure, as well as the mean arterial pressure.

Advantageous Effects

As aforementioned, the blood pressure measurement apparatus of the present invention offers the following merits:

First, patients unpleasantness can be reduced because the blood pressure measurement can be attained with a single apparatus.

Second, patients comfort is provided because the blood pressure can be measured only at one part of the body.

Third, a complete measurement of the blood pressure including the systolic blood pressure and the diastolic blood pressure, as well as the mean arterial pressure is possible.

BRIEF DESCRIPTION OF THE DRAWINGS

FIG. 1 is a block diagram of a blood pressure measurement apparatus according to a first embodiment of the present invention.

FIG. 2 is a boxplot showing the blood pressure measurement result for a control group in accordance with a first embodiment of the present invention.

FIG. 3 shows a picture of the body parts at which the measurement of pulse wave and blood pressure is made in accordance with a first embodiment of the present invention.

FIG. 4 is a graph showing the change of pulse wave amplitude with time at various pressures applied to a body part of the subjects in the test group, in accordance with a first embodiment of the present invention.

FIG. 5 is a graph showing the change of pulse wave amplitude with the pressure applied to a body part of the subjects in the test group at various pressures, in accordance with a first embodiment of the present invention.

FIG. 6 is a graph showing the change of pulse wave amplitude with the pressure applied to various body parts of the subjects in the test group, in accordance with a first embodiment of the present invention.

FIG. 7 is a bar graph showing the elasticity of tissue of the subjects in the test group measured in accordance with a first embodiment of the present invention.

FIG. 8 is a bar graph showing the thickness of the skin, at which the blood vessel is located, of the subjects in the test group, in accordance with a first embodiment of the present invention.

FIG. 9 is a bar graph showing the applied pressure resulting in the maximum pulse pressure of the subjects in the test group, in accordance with a first embodiment of the present invention.

FIG. 10 is a block diagram of a blood pressure measurement apparatus according to a second embodiment of the present invention.

BEST MODE FOR CARRYING OUT THE INVENTION

In order to attain the above-mentioned object, the blood pressure measurement apparatus of the present invention comprises an input unit where at least one value selected from the maximum applied pressure, which is the applied pressure at which the maximum pulse pressure is attained during the pulse pressure measurement at the measurement part, the maximum pulse pressure, which is the pulse pressure at the maximum applied pressure, the depth of blood vessel at the measurement part measured by a pressure sensor, the elasticity of skin tissue at the measurement part and the elasticity of blood vessel at the measurement part is inputted; and a mean arterial pressure calculation unit where the mean arterial pressure is calculated from the input values of the maximum applied pressure, the depth of blood vessel and the elasticity of skin tissue.

Here, the blood pressure measurement apparatus may further comprise: a pulse pressure calculation unit which calculates the pulse pressure, which is a difference of the systolic blood pressure and the diastolic blood pressure from the maximum pulse pressure, the elasticity of skin tissue and the elasticity of blood vessel inputted at the input unit; and a calculation processing unit which calculates the systolic blood pressure and the diastolic blood pressure, respectively, using the mean arterial pressure calculated at the mean arterial pressure calculation unit and the pulse pressure calculated at the pulse pressure calculation unit.

Preferably, the maximum applied pressure is measured tonometrically by monitoring the pulse pressure change at the blood vessel depending on the pressure applied to the measurement part, and the elasticity of skin tissue is calculated from the pressure applied to the measurement part and the vertical displacement of skin caused by applying the pressure.

And, preferably, the mean arterial pressure calculation unit calculates the mean arterial pressure from the depth of blood vessel, the elasticity of skin tissue and the maximum applied pressure inputted at the input unit by the following Math Figure 1:

$$MAP=73.2+4.03 \times ECS-0.0078 \times DB+0.169 \times AP_M \quad \text{MathFigure 1}$$

where MAP is the mean arterial pressure, ECS is the elasticity of skin tissue, DB is the depth of blood vessel and $AP_M$ is the maximum applied pressure at the maximum pulse pressure.

And, preferably, the pulse pressure calculation unit calculates the pulse pressure from the maximum pulse pressure, the elasticity of skin tissue and the elasticity of blood vessel inputted at the input unit by the following Math Figure 2:

$$PP=0.114 \times PP_{max}+1.69 \times ECS-2.04 \times ECB+52.5 \quad \text{MathFigure 2}$$

where PP is the pulse pressure, ECS is the elasticity of skin tissue, ECB is the elasticity of blood vessel and $PP_{max}$ is the maximum pulse pressure.

Also, preferably, the calculation processing unit calculates the systolic blood pressure and the diastolic blood pressure, respectively, from the mean arterial pressure calculated at the mean arterial pressure calculation unit and the pulse pressure calculated at the pulse pressure calculation unit by the following Math Figure 3:

$$MAP=DBP+(SBP-DBP)/3 \quad \text{MathFigure 3}$$

where MAP is the mean arterial pressure, DBP is the diastolic blood pressure, SBP is the systolic blood pressure and (SBP−DBP) is the pulse pressure (PP).

Further, preferably, the maximum applied pressure, the depth of blood vessel, the elasticity of skin tissue, the maximum pulse pressure and the elasticity of blood vessel are measured at the radial artery.

MODE FOR THE INVENTION

Hereinafter, the preferred embodiments of the present invention are described in detail with reference to the attached drawings. It is to be understood that the terms and words used in this description and the claims are not to be interpreted restrictively in common or lexical meaning. Based on the principle that an inventor can properly define the terms to best describe his or her invention, they should be interpreted as conforming to the technical spirit and concept of the present invention.

Accordingly, the embodiments disclosed in this description and the drawings are only preferred examples of the present invention and do not represent the whole technical spirit and concept of the present invention. Thus, it is to be understood that various substitutions and modifications can be made to the invention.

Now, the blood pressure measurement apparatus according to a first embodiment of the present invention is described referring to FIG. 1.

FIG. 1 is a block diagram of a blood pressure measurement apparatus according to a first embodiment of the present invention.

The blood pressure measurement apparatus 100 according to a first embodiment of the present invention comprises an input unit 110 and a mean arterial pressure calculation unit 120.

At the input unit 110, the values of the maximum applied pressure, the depth of blood vessel and the elasticity of skin tissue are inputted. As used herein, the maximum applied pressure means the pressure applied to the measurement part when the maximum pulse pressure is attained.

In accordance with a first embodiment of the present invention, the maximum applied pressure is measured tonometrically by monitoring the pulse pressure change at the blood vessel depending on the pressure applied to the measurement part.

And, the elasticity of skin tissue is calculated from the pressure applied to the measurement part and the vertical displacement of skin caused by the application.

The depth of blood vessel means the thickness from the outer skin to the blood vessel. It can be measured without cutting the body open using such instruments as CT, MRI, X-ray, etc. Alternatively, statistical data considering sex, age, body weight, etc. can be utilized.

The mean arterial pressure calculation unit 120 accepts the values of the maximum applied pressure, the depth of blood vessel and the elasticity of skin tissue from the input unit 110 and corrects the maximum applied pressure based on the depth of blood vessel at the measurement part and the elasticity of skin tissue at the measurement part.

That is, the mean arterial pressure calculation unit 120 in accordance with a first embodiment of the present invention calculates the mean arterial pressure from the values of the maximum applied pressure, the depth of blood vessel and the elasticity of skin tissue by Math Figure 1.

Math Figure 1 was derived from the following experiment.

Experiment was performed for 44 healthy people. Detailed data about the subjects are given in Table 1 below.

TABLE 1

| BMI (kg/m²) | 20 | 20-24 | 24-30 | 30 |
|---|---|---|---|---|
| No. | 5 | 20 | 18 | 1 |
| Age | 20-30 | 30-40 | 40-50 | 50-60 |
| No. | 6 | 9 | 9 | 10 |
| Sex | Male | | Female | |
| No. | 14 | | 30 | |

As a control group, blood pressure measurement was made at the left-side radial artery of the 44 people. Blood pressure was measured using OMRON R6 (OMRON Corporation), which is an oscillometric type blood pressure meter.

For each of the 44 subjects, the systolic blood pressure (SBP) and the diastolic blood pressure (DBP) were measured 5 times and averaged. Mean arterial pressure was calculated from the systolic blood pressure and the diastolic blood pressure by the following Math Figure 3:

MAP=DBP(SBP−DBP)/3 [Math Figure 3]

where MAP is the mean arterial pressure, DBP is the diastolic blood pressure, SBP is the systolic blood pressure and (SBP−DBP) is the pulse pressure (PP).

The result is given in Table 2 and FIG. 2.

FIG. 2 is a boxplot showing the blood pressure measurement result for the control group in accordance with a first embodiment of the present invention.

TABLE 2

| | Maximum | Mean | Minimum |
|---|---|---|---|
| Systolic blood pressure (mmHg) | 155 | 122.98 | 97 |
| Diastolic blood pressure (mmHg) | 103 | 77.57 | 63 |
| Mean pulse pressure (mmHg) | 114.67 | 92.66 | 74.06 |

Then, as a test group, blood pressure measurement was made for the same 44 people using 3-D MAC (Daeyomedi, Co., Ltd.). 3-D MAC is a blood pressure measurement apparatus which tonometrically measures the blood pressure without a cuff.

With 3-D MAC, not only the blood pressure value but also the pulse waveform can be attained. From the pulse waveform, the maximum applied pressure can be found out. In theory, the maximum applied pressure and the mean arterial pressure have the same numerical value. But, in practice, the exact mean arterial pressure cannot be expected from the maximum applied pressure only, due to the discrepancy resulting from the difference of the thickness of blood vessel or the elasticity of skin tissue at the measurement part.

All of the maximum applied pressure, the thickness of blood vessel and the elasticity of skin tissue can be measured conveniently with the 3-D MAC.

In order to find the correlation between the mean arterial pressure, the maximum applied pressure, the thickness of blood vessel and the elasticity of skin tissue, the following experiment was performed using the blood pressure measurement apparatus 100 according to a first embodiment of the present invention.

First, blood pressure was measured at 3 parts of the left-side radial artery and 3 parts of the right-side radial artery of the 44 people using 3-D MAC. The three measurement parts are illustrated in FIG. 3.

FIG. 3 shows the body parts at which the measurement of pulse wave and blood pressure is made in accordance with a first embodiment of the present invention.

Total 228 measurement data were obtained. 198 of them were plotted to derive the Math Figure 1. The remaining 30 data were substituted in the Math Figure 1, which had been derived from the 198 data, to expect the mean arterial pressure, which was compared with the mean arterial pressure measured for the control group.

5 different pressures were applied at the left-side radial artery (part 2 in FIG. 3) of the subjects and the change of pulse wave amplitude was monitored. The voltages measured by 3-D MAC at the different applied pressures are presented in FIG. 4.

FIG. 4 is a graph showing the change of pulse wave amplitude with time at various pressures applied to the body part of the subjects in the test group, in accordance with a first embodiment of the present invention. The abscissa is time (seconds) and the ordinate is the pulse pressure at the blood vessel measured as voltage. The graphs numbered 1, 2, 3, 4 and 5 are pulse pressure measurement results obtained by applying the pressures of 140 g, 200 g, 90 g, 45 g and 250 g, respectively, to the same body part of the same person.

Then, based on the amplitude values depending on the pressures applied to the body part of the subjects, the graphs presented in FIG. 5 and FIG. 6, were obtained.

FIG. 5 is a graph showing the change of pulse wave amplitude with the pressure applied to a body part of the subjects in the test group at various pressures, in accordance with a first embodiment of the present invention. And, FIG. 6 is a graph showing the change of pulse wave amplitude with the pressure applied to various body parts of the subjects in the test group, in accordance with a first embodiment of the present invention.

In FIG. 5, the abscissa is the pressure applied to the body part and the ordinate is the pulse pressure measured at the blood vessel located at the body part.

The maximum applied pressure $AP_M$, which is the applied pressure when the maximum voltage value h1 is obtained, is given in the figure. That is, from FIG. 5, it can be seen that the maximum applied pressure measured at the body part of the subjects in the test group in accordance with a first embodiment of the present invention is 140.

In FIG. 6, the abscissa is the pressure applied to the body part and the ordinate is the pulse pressure measured at the blood vessel located at the body part. In the figure, the graphs numbered 1, 2, 3, 4, 5 and 6 are results obtained from different body parts.

From FIG. 6, it can be seen that maximum applied pressure differs in various body parts. It is because the depth of blood vessel and the elasticity of skin tissue are different from one body part to another.

The values of the depth of blood vessel, the elasticity of skin tissue and the maximum applied pressure of the subjects are presented in FIGS. 7 to 9.

FIG. 7 is a bar graph showing the elasticity of tissue of the subjects in the test group measured in accordance with a first embodiment of the present invention. FIG. 8 is a bar graph showing the thickness of the skin, at which the blood vessel is located, of the subjects in the test group, in accordance with a first embodiment of the present invention. And, FIG. 9 is a bar graph showing the applied pressure resulting in the maximum pulse pressure of the subjects in the test group, in accordance with a first embodiment of the present invention.

In FIG. 7, the abscissa is the elasticity of skin tissue (g/□ Index) and the ordinate is the number of subjects. The total number of the subjects was 198. The average of the skin tissue elasticity was 0.8854 g/□ Index and the standard deviation was 0.2295.

In FIG. 8, the abscissa is the thickness of blood vessel (10□) and the ordinate is the number of subjects. The total number of the subjects was 198. The average of the thickness of blood vessel was 551.6×10□ the standard deviation was 351.9.

In FIG. 9, the abscissa is the maximum applied pressure (g) and the ordinate is the number of subjects. The total number of the subjects was 198. The average of the maximum pulse pressure was 127.4 g and the standard deviation was 34.34.

From the graphs shown in FIGS. 5 to 9, the Math FIG. 1 was derived by using a data analysis software.

When different pressures are applied to a measurement part on the skin of a subject, the pulse pressure at the blood vessel is varied depending on the magnitude of the applied pressure.

As described earlier, the maximum applied pressure at which the maximum pulse pressure is attained can be expressed as a function of the subject, the elasticity of skin tissue, the depth of blood vessel, and so forth.

It is to be understood that, using this physical and logical intrinsic relationships along with the statistical data obtained from the test group, including the maximum applied pressure, the depth of blood vessel, the elasticity of skin tissue, etc., the mean arterial pressure can be expressed by the maximum applied pressure, the depth of blood vessel and the elasticity of skin tissue.

By increasing the number of test samples, a more precise statistical result can be derived. And, with the help of MINITA P14, a statistical analysis tool widely adopted for systematic statistical operation and analysis, the statistical results can be summarized into a mathematical formula.

That is, based on the statistical data illustrated in FIGS. 7 to 9, a mathematical formula for calculating the mean arterial pressure can be derived.

In order to verify the exactness of the mean arterial pressure calculated by such a formula, the average and the standard deviation were compared with the result obtained using the commonly used cuff type blood pressure meter. As a result, the mean arterial pressure calculated from the elasticity of skin tissue, the depth of blood vessel and the maximum applied pressure showed an accuracy of 92.1%.

The result of comparing the mean arterial pressure calculated based on the data and the mathematical formula with the mean arterial pressure measured from the control group is given in Table 3 below.

The change of amplitude at the blood vessel was largest when the applied pressure was 140 g.

TABLE 3

| Difference of average (mmHg) | Standard deviation (mmHg) |
|---|---|
| −3.183 | 5.133 |

As seen in Table 3, the difference of the average of blood pressure was as small as −3.183 mmHg and the standard deviation was 5.133 mmHg.

The result given in Table 3 is significant, considering that the American National Standard for Electronic or Automated Mercury Manometers specify that the difference of average be 5 mmHg or smaller and the standard deviation be 8 mmHg or smaller. Hence, the apparatus of the present invention is proved to be an effective blood pressure meter.

Hereinafter, a blood pressure measurement apparatus in accordance with a second embodiment of the present invention is described referring to FIG. 10.

FIG. 10 is a block diagram of a blood pressure measurement apparatus according to a second embodiment of the present invention.

Referring to FIG. 10, the blood pressure measurement apparatus 200 according to a second embodiment of the present invention comprises an input unit 210, a mean arterial pressure calculation unit 220, a pulse pressure calculation unit 230 and a calculation processing unit 240.

At the input unit 210, the values of the maximum applied pressure, the maximum pulse pressure, the depth of blood vessel, the elasticity of skin tissue and the elasticity of blood vessel are inputted.

Here, the maximum applied pressure, the depth of blood vessel and the elasticity of skin tissue are obtained by the same method as in the aforesaid first embodiment of the present invention.

The mean arterial pressure calculation unit 220 accepts the values of the maximum applied pressure, the depth of blood vessel and the elasticity of skin tissue from the input unit 210 and corrects the maximum applied pressure based on the depth of blood vessel at the measurement part and the elasticity of skin tissue at the measurement part.

That is, the mean arterial pressure calculation unit 220 in accordance with a second embodiment of the present invention calculates the mean arterial pressure from the values of the maximum applied pressure, the depth of blood vessel and the elasticity of skin tissue by Math Figure 1.

The maximum pulse pressure means the pulse pressure at which the maximum applied pressure is obtained. The values of the maximum applied pressure and the maximum pulse pressure were obtained tonometrically, as in the first embodiment of the present invention, using 3-D MAC.

However, a precise pulse pressure could not be obtained from the maximum pulse pressure obtained using the 3-D MAC.

That is, the pulse pressure measured with a conventional blood pressure meter and the pulse pressure obtained using the 3-D MAC did not show a 1:1 correlation, which indicates that the pulse pressure is not correctly read by the 3-D MAC.

From this, it can be seen that in the blood pressure measurement apparatus according to a second embodiment of the present invention, the pulse pressure calculated from "(the systolic blood pressure)−(the diastolic blood pressure)" is affected by the physical properties of the body part at which the measurement is made and that the maximum pulse pressure has to be corrected considering the elasticity of skin tissue and the elasticity of blood vessel in order to attain a more accurate pulse pressure value.

From the fact that the elasticity of skin tissue affects the pulse pressure, it can also be indicated that the elasticity of blood vessel may be another factor affecting the pulse pressure.

The elasticity of blood vessel was measured by AI (augmentation index), which is a tonometric technique currently adopted in the diagnosis of cardiovascular diseases in the US, Australia, Japan, and so forth. AI is a simple analysis index for reflection wave and is a measure of the arterial elasticity. It is used to diagnose arteriosclerosis and other diseases.

The principle of AI is as follows. An incident wave generated at the aorta is reflected at the peripheral blood vessel and comes back as a reflected wave. The AI is calculated by dividing the difference between a magnitude of the pulse wave at the time of occurrence of the peak of the incident-wave component and a magnitude of the pulse wave at the time of occurrence of the peak of the reflected-wave component, by a pulse pressure of the pulse wave. The stiffer the artery, the faster the reflected wave comes back, resulting in the change of the time of the peak occurrence.

In the experiment, the R-AI, which is the AI at the radial artery, was used. The R-AI is calculated in percentage by dividing the difference of the systolic blood pressure of the second peak (SBP2) and the diastolic blood pressure (DBP) by the difference of the systolic blood pressure of the first peak (SBP) and the diastolic blood pressure, and then multiplying 100.

That is, the R-AI can be expressed by the following Math Figure 4:

$$\{(SBP2-DBP)/(SBP-DBP)\} \times 100 \qquad \text{MathFigure 4}$$

where DBP is the diastolic blood pressure, SBP is the systolic blood pressure of the first peak and SBP2 is the systolic blood pressure of the second peak.

The following experiment was performed for 50 people aged between 20 and 30 with no cardiovascular diseases, in order to derive the Math Figure for calculating the pulse pressure. The Math Figure 2 was derived from a coefficient of the regression Math Figure attained by the experiment and the pulse pressure was calculated using the Math Figure 2.

Detailed data about the healthy 50 subjects are listed in Table 4 below.

TABLE 4

| BMI (kg/m$^2$) | 20 | 20-24 | 24-30 | 30 |
|---|---|---|---|---|
| No. | 3 | 27 | 26 | 4 |
| Age | 20-22 | 22-24 | 24-26 | 26-28 |
| No. | 1 | 2 | 1 | 31 |
| Sex | Male | | Female | |
| No. | 38 | | 12 | |

For the 50 people, blood pressure measurement was made using a conventional mercury manometer and the 3-D MAC. The measurement part was left-side forearm for the mercury manometer and a portion of the left-side radial artery for the 3-D MAC.

Measurement was made with a mercury manometer and then immediately with 3-D MAC. After 5 minutes of rest, measurement was made again with the blood pressure and then immediately with the 3-D MAC. Because the blood pressure at the aorta is what is to be measured in this experiment, the fact that the measurement part is forearm or wrist does not make any difference at all The average values of the systolic blood pressure (SBP) and the diastolic blood pressure (DBP) of the 50 subjects are summarized in Table 5.

TABLE 5

| | Maximum | Average | Minimum |
|---|---|---|---|
| Systolic blood pressure (mmHg) | 138 | 123 | 98 |
| Diastolic blood pressure (mmHg) | 90 | 78 | 68 |
| Mean arterial pressure (mmHg) | — | 45 | — |

Referring to FIG. 5, since the abscissa is the pressure applied to the body part and the ordinate is the pulse pressure measured at the blood vessel located at the body part, the point where the largest voltage value (h1) is attained is the maximum pulse pressure ($PP_{max}$), or the pulse pressure where the maximum applied pressure is attained.

The graph of FIGS. 5 was analyzed using a data analysis software. And, using a statistics program, the pulse pressure measured using the blood pressure meter and the maximum pulse pressure obtained using the 3-D MAC were regressed to derive the Math Figure 2.

The pulse pressure calculation unit 230 accepts the values of the maximum pulse pressure, the elasticity of skin tissue, and the elasticity of blood vessel from the input unit 210 and corrects the maximum pulse pressure based on the elasticity of skin tissue at the measurement part and the elasticity of blood vessel at the measurement part.

That is, the pulse pressure calculation unit 230 in accordance with a second embodiment of the present invention calculates the pulse pressure from the maximum pulse pressure, the elasticity of skin tissue and the elasticity of blood vessel by Math Figure 2.

In order to verify the exactness of the maximum pulse pressure calculated by Math Figure 2, the average and the standard deviation were compared with the result obtained using the commonly used cuff type blood pressure meter. The accuracy was 87.3%.

The result of comparing the maximum pulse pressure calculated based on the data and the Math Figure 2 with the maximum pulse pressure measured using the cuff type blood pressure meter is given in Table 6 below.

TABLE 6

| Difference of average (mmHg) | Standard deviation (mmHg) |
|---|---|
| 3.525 | 4.118 |

As seen in Table 6, the difference of the average of blood pressure was as small as 3.525 mmHg and the standard deviation was 4.118 mmHg.

The result given in Table 6 is significant, considering that the American National Standard for Electronic or Automated Mercury Manometers specify that the difference of average be 5 mmHg or smaller and the standard deviation be 8 mmHg or smaller. Hence, the apparatus of the present invention is proved to be an effective blood pressure meter.

The calculation processing unit 240 calculates the systolic blood pressure and the diastolic blood pressure from the mean arterial pressure calculated at the mean arterial pressure calculation unit 220 and the pulse pressure calculated at the pulse pressure calculation unit 230 by Math Figure 3.

Thus, not only the mean arterial pressure, but also the systolic blood pressure and the diastolic blood pressure were obtained.

Although the present invention has been described using exemplary embodiments and drawings, the present invention is not limited thereto and may be variously modified or changed within the spirit and scope of the invention defined by the accompanying claims by those ordinarily skilled in the art.

The invention claimed is:

1. A blood pressure measurement apparatus comprising:
    an input unit for inputting values including a maximum applied pressure, a depth of blood vessel at a measurement part measured by a pressure sensor, and an elasticity of skin tissue at the measurement part; and
    a mean arterial pressure calculation unit where a mean arterial pressure is calculated from input values of the maximum applied pressure, the depth of blood vessel and the elasticity of skin tissue.

2. The blood pressure measurement apparatus of claim 1, wherein the input unit is capable of accepting input values further including an elasticity of blood vessel at the measurement part, and the maximum pulse pressure, wherein the maximum pulse pressure is the pulse pressure at the maximum applied pressure, and further wherein the maximum applied pressure is the applied pressure at which the maximum pulse pressure is attained during a pulse pressure measurement at the measurement part.

3. The blood pressure measurement apparatus of claim 2, further including:
    a pulse pressure calculation unit which calculates the pulse pressure, which is a difference of systolic blood pressure and diastolic blood pressure, from the maximum pulse pressure, the elasticity of skin tissue and the elasticity of blood vessel inputted at the input unit; and
    a calculation processing unit which calculates the systolic blood pressure and the diastolic blood pressure, respectively, using the mean arterial pressure calculated at the mean arterial pressure calculation unit and the pulse pressure calculated at the pulse pressure calculation unit.

4. The blood pressure measurement apparatus of claim 2, wherein the maximum applied pressure is measured tonometrically by monitoring the pulse pressure change of a blood vessel depending on the pressure applied to the measurement part, and the elasticity of skin tissue is calculated from the pressure applied to the measurement part and the vertical displacement of skin caused by applying the pressure.

5. The blood pressure measurement apparatus of claim 3, wherein the maximum applied pressure is measured tonometrically by monitoring the pulse pressure change of a blood vessel depending on the pressure applied to the measurement part, and the elasticity of skin tissue is calculated from the pressure applied to the measurement part and the vertical displacement of skin caused by applying the pressure.

6. The blood pressure measurement apparatus of claim 2, wherein the mean arterial pressure calculation unit calculates the mean arterial pressure from the depth of blood vessel, the elasticity of skin tissue and the maximum applied pressure inputted at the input unit by the equation:

$$MAP=73.2+4.03\times ECS-0.0078\times DB+0.169\times APM$$

where MAP is the mean arterial pressure, ECS is the elasticity of skin tissue, DB is the depth of blood vessel and AP is the maximum applied pressure at the M maximum pulse pressure.

7. The blood pressure measurement apparatus of claim 3, wherein the mean arterial pressure calculation unit calculates the mean arterial pressure from the depth of blood vessel, the elasticity of skin tissue and the maximum applied pressure inputted at the input unit by the equation:

$$MAP=73.2+4.03\times ECS-0.0078\times DB+0.169\times AP_M$$

where MAP is the mean arterial pressure, ECS is the elasticity of skin tissue, DB is the depth of blood vessel and AP is the maximum applied pressure at the M maximum pulse pressure.

8. The blood pressure measurement apparatus of claim 3, wherein the pulse pressure calculation unit calculates the pulse pressure from the maximum pulse pressure, the elasticity of skin tissue and the elasticity of blood vessel inputted at the input unit by the equation:

$$PP=0.114\times PP_{max}+1.69\times ECS-2.04\times ECB+52.5$$

where PP is the pulse pressure, ECS is the elasticity of skin tissue, ECB is the elasticity of blood vessel and $PP_{max}$ is the maximum pulse pressure.

9. The blood pressure measurement apparatus of claim 3, wherein the calculation processing unit calculates the systolic blood pressure and the diastolic blood pressure, respectively, from the mean arterial pressure calculated by the mean arterial pressure calculation unit and the pulse pressure calculated by the pulse pressure calculation unit using the equation:

$$MAP=DBP+(SBP-DBP)/3$$

where MAP is mean arterial pressure, DBP is diastolic blood pressure, SBP is systolic blood pressure, and (SBP−DBP) is pulse pressure (PP).

10. The blood pressure measurement apparatus of claim 2, wherein the maximum applied pressure, the depth of blood vessel, the elasticity of skin tissue, the maximum pulse pressure and the elasticity of blood vessel are measured at the radial artery.

11. The blood pressure measurement apparatus of claim 3, wherein the maximum applied pressure, the depth of blood vessel, the elasticity of skin tissue, the maximum pulse pressure and the elasticity of blood vessel are measured at the radial artery.

* * * * *